United States Patent [19]
Spindel et al.

[11] Patent Number: 5,439,884
[45] Date of Patent: Aug. 8, 1995

[54] METHOD OF CONTROLLING FERTILIZATION USING BOMBESIN OR ITS AGONIST

[75] Inventors: Eliot R. Spindel, Lake Oswego; Srinivasa R. Nagalla, Portland; Srinivasan Vijayaraghavan, Beaverton; Anthony Archibong, Portland, all of Oreg.

[73] Assignee: Oregon Regional Primate Research Center, Beaverton, Oreg.

[21] Appl. No.: 919,731

[22] Filed: Jul. 27, 1992

[51] Int. Cl.⁶ .................. A61K 38/10; A61K 38/17
[52] U.S. Cl. ................................ 514/12; 514/12; 514/14; 514/15
[58] Field of Search ............... 514/14, 13, 12, 15

[56] References Cited
U.S. PATENT DOCUMENTS 5,112,596 5/1992 Malfroy-Cahne ............... 514/17 X

OTHER PUBLICATIONS

L. Gnessi et al., "Identificaiton of immunoreactive gastrin-releasing peptide related substances in adult rat leydig cells" Endocrinology 124:558, 1989.
L. Gnessi et al., "Isolation of a human seminal plasma peptide with bombesin-like activity" Fertil. Steril. 51:1034, 1989.
L. Gnessi et al., "Gastrin-releasing peptide-like immunoreactivity in porcine follicular fluid and ovary" Mol. Cell Endocrinol. 66:115, 1989.

*Primary Examiner*—Howard E. Schain
*Attorney, Agent, or Firm*—Fish & Richardson

[57] ABSTRACT

A method of promoting or blocking fertilization, which method includes the step of contacting sperm either at the time of sperm capacitation or at the time of egg fertilization with an effective amount of bombesin or its analog capable of stimulating or inhibiting the acrosome reaction.

16 Claims, 3 Drawing Sheets

FIG. 1A  GRP

FIG. 1B  GRP RECEPTOR

METHOD OF CONTROLLING FERTILIZATION USING BOMBESIN OR ITS AGONIST

STATEMENT AS TO FEDERALLY SPONSORED RESEARCH

This invention was made with support from the National Institute of Health (Grant No. R01-CA39237). Accordingly, the U.S. government has certain rights in the invention.

FIELD OF THE INVENTION

This invention relates to the method of promoting or blocking fertilization. More particularly, it relates to the use of fertilization and contraceptive agents.

BACKGROUND OF THE INVENTION

At present, the overall success rate for in vitro fertilization is approximately 20–25%. This figure includes multiple attempts (up to 3-4 times by some couples) to succeed. Thus, any process which can increase the efficiency of fertilization will have significant utility for in vitro fertilization procedures.

On the other hand, it is estimated that there are 1.5 to 2 million pregnancies that occur in the United States alone because of failures in contraception. Failure rates of vaginal contraceptives such as foam or jelly, either alone or in combination with condoms or diaphragm, range from 2–20% per year depending on conditions and the study cited. See Developing New Contraceptive: Obstacles and Opportunities, Washington D.C., National Academy Press (1990). Therefore, any minor improvement in the efficiency of contraceptives, thousands of accidental or unwanted pregnancies could be prevented per year.

Bombesin, a tetradecapeptide amide first isolated from the skin of the frog Bombina bombina, is a potent mitogen for mouse Swiss 3T3 fibroblast cells. It also stimulates secretion for guinea pig pancreatic acini. Bombesin-like peptides are produced and secreted by human small cell lung cancer cells ("SCLC") and exogenously added bombesin-like peptides can stimulate the growth of human SCLC cells in vitro.

Gastrin releasing peptide ("GRP") is a 27 amino acid peptide amide first isolated from the porcine gut. The C-terminal amino acid sequence of GRP is almost identical to that of bombesin. Neuromedin C is a decapeptide amide, the structure of which is identical to the last ten amino acids in the C-terminal region of GRP. Both GRP and Neuromedin C possess bombesin-like properties. Other bombesin-like peptides include litorin and Neuromedin B.

It has not been reported hitherto that bombesin or bombesin-like peptides (e.g., GRP) are capable of increasing or decreasing the efficiency of fertilization of eggs by sperm.

SUMMARY OF THE INVENTION

Uncommon Abbreviations:
Chx-Ala=3-cyclohexylalanine
pGlu=pyroglutamic acid
Nle=norleucine
HyPro=hydroxyproline
Sar=sarcosine
Aza-Tyr=3-(5-hydroxy-2-pyridyl)-alanine
Cpa=p-chlorophenylalanine
X-Phe=p-, o-, or m- substituted phenylalanine
$F_5$-Phe=pentafluorophenylalanine
$\beta$-Nal=3-($\beta$-naphthyl)-alanine
Met-oxide=methionine oxide
1- or 3-methyl-His=histidine with a methyl substituent at $N^1$ or $N^3$ of its heterocyclic ring.
Tcc=1,2,3,4-tetrahydro-2-carboline-3-carboxylic acid
Tic=1,2,3,4-tetrahydro-2-carboline-3-yl-carboxylic acid
Tip=4,5,6,7-tetrahydro-1H-imidazo[c]pyridine-6-carboxylic acid
Oic=(3aS, 7aS)-octahydroindol-2-yl-carboxylic acid
Tpi=2,3,4,9-tetrahydro-1H-pyrido[3,4-b]indol-3-carboxylic acid
Lys(Z)=$N^6$-(benzyloxycarbonyl)-lysine
Lys(COCH$_3$)=$N^6$-acetyllysine
Lys(COPh)=$N^6$-benzoyllysine
Lys(COCH$_2$Ph)=$N^6$-(phenylacetyl)-lysine
Lys(COCH$_2$CH$_2$Ph)=$N^6$-(3-phenylpropionyl)-lysine For fertilization to occur, sperm must undergo an exocytotic process called the acrosome reaction which enables sperm to penetrate the external layers of the ova. For the acrosome reaction to occur, sperm must undergo the process of capacitation. (The operational definition of capacitation is simply the ability of sperm to undergo the acrosome reactions) Applicants have now discovered that bombesin or its analog is capable of promoting or inhibiting the acrosome reaction, as well as the egg fertilization.

Therefore, the present invention, in general, features a method of promoting or blocking fertilization by contacting sperm either at the time of sperm capacitation or at the time of egg fertilization with an effective amount of bombesin or its analog capable of stimulating or inhibiting the acrosome reaction.

The method can be applied to in vitro fertilization or artificial insemination for promoting fertilization. For example, bombesin or a suitable bombesin analog [e.g., bombesin (6–14), GRP, or GRP (18–27)] can be administered vaginally to a female subject, or administered systemically or locally to a male subject. Local administration to a male subject can be achieved by implantation of a biodegradable or retrievable polymer formulation in the scrotum. An example of a suitable biodegradable polymer for such use is polylactide-glycolide polymer carrier. E.g., see Tissier B. Recent Progress on GnRH and Gonadal Peptides, pp. 159–168, Bouchard P. et al. eds. Elsevier, Paris (1990), which is hereby incorporated by reference. Silicone, on the other hand, can be used to prepare a retrievable polymer formulation to be implanted in a male subject. Note the term "subject" herein refers to either a human being or an animal. In other words, both medical and veterinary applications are within the scope of the present invention.

The method can also be used to block fertilization by administering vaginally to a female subject a suitable bombesin analog, e.g., in a formulation consisting of sponge, foam, jelly, and a biocompatible matrix (such as a barrier type of contraceptive device). Alternatively, the bombesin analog can be administered to a male subject, either systemically or locally.

The dose of bombesin or its analog used according to the present invention varies depending upon the manner of administration and the condition of the subject to be treated, and ultimately will be decided by the attending physician or veterinarian. Such amount of the active peptide compound as determined by the attending physician or veterinarian is referred to herein as an "effective amount". A typical administration method is oral administration or parenteral administration.

The structure of bombesin is as follows:

H-pGlu-Gln-Arg-Leu-Gly-Asn-Gln-Trp-Ala-Val-Gly-His-Leu-Met-NH₂ (SEQ ID NO:1)

The structure of GRP is as follows:

H-Ala-Pro-Val-Ser-Val-Gly-Gly-Gly-Thr-Val-Leu-Ala-Lys-Met-Tyr-Pro-Arg-Gly-Asn-His-Trp-Ala-Val-Gly-His-Leu-Met-NH₂ (SEQ ID NO:2).

The bombesin analogs of this invention include bombesin fragments [e.g., bombesin (6–14)], GRP, GRP fragments [e.g., GRP (18–27)], and numerous synthetic compounds disclosed in the art including the publications to be discussed immediately below [e.g., Tpi⁶, Leu¹³-ψ(CH₂—NH)-Leu¹⁴ bombesin (6–14)]. (Note that pseudopeptide bond and the type of the bond is indicated in the parenthesis following it.) Naturally occurring compounds such as Neuromedin B or Neuromedin C, either in human or in other organisms, are also included.

Several bombesin antagonists are known whereby the structure of the undecapeptide, substance P, is modified by the replacement of several of its L-amino acids with D-amino acids. See Jensen et al. Nature 309:61 (1984); Zachary et al. Proc. Natl. Acad. Sci. USA 82:7616 (1985); and Heinz-Erian et al. Gastroenterology 90:1455 (1986). A few bombesin antagonists derived from the structure of bombesin have also been disclosed. See Markl et al. Peptides 2, Suppl. 2:169 (1981) and Heinz-Erian et al. Amer. J. Physiol. 252:G439 (1987). In addition, it has been disclosed that bombesin analog containing a pseudopeptide bond, e.g., [Leu¹³-ψ(CH₂—NH)-Leu¹⁴] bombesin and Ala⁹-ψ(CH₂—NH)-Val¹⁰-Leu¹⁴] bombesin, are also bombesin antagonists. See Coy et al. Regulatory Peptides 19:105 (1987); International Symposium on Bombesin-like Peptides, Rome, October, 1987; and Coy et al. J. Biol. Chem. 263:5056 (1988). Furthermore, certain Neuromedin C derivatives have been found to be potent bombesin antagonists. See EP Application 0 345 990 A2 (1989). Several bombesin agonists are disclosed in Wang et al. J. Biol. Chem. 265:15695 (1990).

All of the just-mentioned articles and the publications listed below contain bombesin analogs which can be used to practice the present invention and are hereby incorporated by reference.

Coy et al. Peptides, Proceedings of the Eleventh Amer. Peptide Symposium, Ed. by Rivier et al. ESCOM, pp. 65–67 (1990);
Wang et al. J. Biol. Chem. 265:15695 (1990);
Mahmoud et al. Cancer Research 51:1798 (1991);
Wang et al. Biochemistry 29:616 (1990);
Heimbrook et al., "Synthetic Peptides: Approaches to Biological Problems", UCLA Symposium on Mol and Cell. Biol. New Series, Vol. 86, ed. Tam and Kaiser;
Martinez et al., J. Med. Chem. 28:1874 (1985);
Gargosky et al., Biochem. J. 247:427 (1987);
Dubreuil et al., Drug Design and Delivery, Vol 2:49, Harwood Academic Publishers, GB (1987);
Heikkila et al., J. Biol. Chem. 262:16456 (1987);
Caranikas et al., J. Med. Chem. 25:1313 (1982);
Saeed et al., Peptides 10:597 (1989);
Rosell et al., Trends in Pharmacological Sciences 3:211 (1982);
Lundberg et al., Proc. Nat. Aca. Sci. 80:1120, (1983);
Engberg et al., Nature 293:222 (1984);
Mizrahi et al., Euro. J. Pharma. 82:101 (1982);
Leander et al., Nature 294:467 (1981);
Woll et al., Biochem. Biophys. Res. Comm. 155:359 (1988);
Rivier et al., Biochem. 17:1766 (1978);
Cuttitta et al., Cancer Surveys 4:707 (1985);
Aumelas et al., Int. J. Peptide Res. 30:596 (1987);
Szepeshazi. et al., Cancer Resaerch 51:5980 (1991);
U.S. Pat. No. 5,028,692;
U.S. Pat. No. 4,943,561;
U.S. Pat. No. 4,207,311;
U.S. Pat. No. 5,068,222;
U.S. Pat. No. 5,081,107.

Preferably, the bombesin analog of this invention has the following formula:

wherein

A¹ is a D-amino acid selected from the group consisting of Phe and X-Phe (where X is F, Cl, Br, NO₂, OH, or CH₃), Tcc, Tic, Tip, Oic, and Tpi, or is deleted;

A² is Gln, His, 1-methyl-His, or 3-methyl-His;

A³ is a D- or L-amino acid selected from the group consisting of β-Nal, Trp, Phe, and X-Phe, where X is F, Cl, Br, NO₂, OH, or CH₃;

A⁴ is Ala, Val, Leu, Ile, Nle, or α-aminobutyric acid;

A⁵ is Val, Ala, Leu, Ile, Nle, Thr, or α-aminobutyric acid;

A⁶ is Gly, Sar, or a D-amino acid selected from the group consisting of Ala, N-methyl-Ala, Trp, and β-Nal;

A⁷ is His, 1-methyl-His, or 3-methyl-His;

A⁸ is Leu, Ile, Val, Nle, α-aminobutyric acid, Trp, β-Nal, Chx-Ala, Phe, or X-Phe, where X is F, Cl, Br, NO₂, OH, or CH₃;

A⁹ is Met, Met-oxide, Leu, Ile, Nle, α-aminobutyric acid, or Cys;

each R₁ and R₂, independently, is H, C₁₋₂₀ alkyl, C₂₋₂₀ alkenyl, C₂₋₂₀ alkynyl, phenyl, naphthyl, C₇₋₂₀ phenylalkyl, C₁₁₋₂₀ naphthylalkyl, COE₁ or COOE₁ (where E₁ is C₁₋₂₀ alkyl, C₂₋₂₀ alkenyl, C₂₋₂₀ alkynyl, phenyl, naphthyl, C₇₋₂₀ phenylalkyl, C₁₁₋₂₀ naphthylalkyl, pyridyl, or indolyl); provided that when either R₁ or R₂ is COE₁ or COOE₁, the other must be H; and R₃ is OH, NH₂, C₁₋₂₀ alkoxy, C₇₋₂₀ phenylalkoxy, or C₁₁₋₂₀ naphthylalkoxy.

Particular preferred analogs covered by Formula (A) are those in which

A¹ is D-Phe, D.-Cpa, or deleted;
A² is Gln, His, 1-methyl-His, or 3-methyl-His;
A³ is Trp;
A⁴ is Ala;
A⁵ is Val;
A⁶ is Sar, Gly, D-Phe, or D-Ala;
A⁷ is His;
A⁸ is Leu, Phe, Chx-Ala, or Cys; and
A⁹ is Met, Leu, Ile, Nle, or Cys.

Also preferably, the bombesin analog of this invention has the following formula:

$$\begin{array}{c} R_1 \\ \phantom{R}\diagdown \\ \phantom{RR} A^0-A^1-A^2-Trp-A^4-A^5-A^6-A^7-W \\ \phantom{R}\diagup \\ R_2 \end{array} \quad (B)$$

wherein $A^0$ is pGlu, Gly, Nle, e-aminobutyric acid, a D-amino acid selected from the group consisting of Ala, Val, Gln, Asn, Leu, Ile, Met, Phe, X-Phe (where X is F, Cl, Br, $NO_2$, OH, or $CH_3$), Trp, Cys, and $\beta$-Nal, or is deleted;

$A^1$ is a D- or L-amino acid selected from the group consisting of pGlu, Nle, $\alpha$-aminobutyric acid, or a D-amino acid selected from the group consisting of Ala, Val, Gln, Asn, Leu, Ile, Met, Aza-Tyr, Phe, X-Phe (where X is F, Cl, Br, $NO_2$, OH, or $CH_3$), $F_5$-Phe, Trp, Cys, Tcc, Tic, Tip, Oic, Tpi, and $\beta$-Nal, or is deleted;

$A^2$ is pGlu, Gly, Ala, Val, Gln, Asn, Leu, Ile, Met, Phe, X-Phe (where X is F, Cl, Br, $NO_2$, OH, or $CH_3$), Trp, Cys, $\beta$-Nal, His, 1-methyl-His, or 3-methyl-His;

$A^4$ is Ala, Val, Gln, Asn, Gly, Leu, Ile, Nle, $\alpha$-aminobutyric acid, Met, Phe, X-Phe (where X is F, Cl, Br, $NO_2$, OH, or $CH_3$), Trp, Cys, or $\beta$-Nal;

$A^5$ is Gln, Asn, Gly, Ala, Leu, Ile, Nle, $\alpha$-aminobutyric acid, Met, Val, Phe, X-Phe (where X is F, Cl, Br, OH, or $CH_3$), Trp, Thr, or $\beta$-Nal;

$A^6$ is Sar, Gly, or a D-amino acid selected from the group consisting of Ala, N-methyl-Ala, Val, Gln, Asn, Leu, Ile, Met, Phe, X-Phe (where X is F, Cl, Br, $NO_2$, OH, or $CH_3$), Trp, Cys, and $\beta$-Nal;

$A^7$ is 1-methyl-His, 3-methyl-His, His, Lys (Z), Lys(-$COCH_3$), Lys(COPh), Lys($COCH_2Ph$), or Lys(-$COCH_2CH_2Ph$);

each $R_1$ and $R_2$, independently, is H, $C_{1-20}$ alkyl, $C_{2-20}$ alkenyl, $C_{2-20}$ alkynyl, phenyl, naphthyl, $C_{7-20}$ phenylalkyl, $C_{11-20}$ naphthylalkyl, $COE_1$ or $COOE_1$ (where $E_1$ is $C_{1-20}$ alkyl, $C_{3-20}$ alkenyl, $C_{3-20}$ alkynyl, phenyl, naphthyl, $C_{7-20}$ phenylalkyl, $C_{11-20}$ naphthylalkyl, pyridyl, or indolyl), and is bonded to the nitrogen of the $\alpha$-amino group of the N-terminal amino acid residue; provided that when either $R_1$ or $R_2$ is $COE_1$ or $COOE_1$, the other must be H;

W is one of the following groups:

$$\begin{array}{ccc} Z_1 & & O \\ | & & \| \\ -NH-CH-R_3-C-V_1, \end{array} \quad (I)$$

wherein $R_3$ is $CHR_{20}-(CH_2)_{n1}$ (where $R_{20}$ is either of H or OH; and n1 is either of 1 or 0), or is deleted, and $Z_1$ is the identifying group of any of the amino acids Gly, Ala, Val, Leu, Ile, Ser, Asp, Asn, Glu, Gln, Phe, X-Phe (where X is F, Cl, Br, $NO_2$, OH, or $CH_3$), $F_5$-Phe, Trp, Cys, Met, Pro, HyPro, Chx-Ala, or $\beta$-Nal; and $V_1$ is either $OR_4$, or $$-N\begin{array}{c} R_5 \\ \diagdown \\ \diagup \\ R_6, \end{array}$$

where $R_4$ is $C_{1-20}$ alkyl, $C_{3-20}$ alkenyl, $C_{3-20}$ alkynyl, phenyl, naphthyl, $C_{7-20}$ phenylalkyl, $C_{11-20}$ naphthylalkyl and each $R_5$ and $R_6$, independently, is H, $C_{1-20}$ alkyl, $C_{3-20}$ alkenyl, $C_{3-20}$ alkynyl, phenyl, naphthyl, $C_{7-20}$ phenylalkyl, $C_{11-20}$ naphthylalkyl, $C_{1-20}$ acyl, or, $$-N\begin{array}{c} R_{22} \\ \diagdown \\ \diagup \\ H \end{array},$$

where $R_{22}$ is H, $C_{1-20}$ alkyl, $C_{3-20}$ alkenyl, $C_{3-20}$ alkynyl, phenyl, naphthyl, $C_{7-20}$ phenylalkyl, $C_{11-20}$ naphthylalkyl, or $C_{1-20}$ acyl; provided that, when either $R_5$ or $R_6$ is $-NHR_{22}$, the other is H;

$$\begin{array}{ccccc} R_4 & Z_2 & & Z_3 & O \\ | & | & & | & \| \\ -N-CH-R_5-CH-C-V_2, \end{array} \quad (II)$$

wherein $R_5$ is $CH_2-NH$, $CH_2-S$, $CH_2-S(O)$, $CH_2-O$, $CO-CH_2$, $CH_2-CO$, or $CH_2-CH_2$, and each $Z_2$ and $Z_3$, independently, is the identifying group of Gly, Ala, Val, Leu, Ile, Ser, Asp, Asn, Glu, Gln, $\beta$-Nal, Phe, X-Phe (where X is F, Cl, Br, $NO_2$, OH, or $CH_3$), $F_5$-Phe, Trp, Cys, Met, Pro, HyPro, or Chx-Ala; and $V_2$ is either $OR_6$ or $$-N\begin{array}{c} R_7 \\ \diagdown \\ \diagup \\ R_8, \end{array}$$

where each $R_4$, $R_6$, $R_7$, and $R_8$, independently, is H, $C_{1-20}$ alkyl, $C_{2-20}$ alkenyl, $C_{2-20}$ alkynyl, phenyl, naphthyl, $C_{7-20}$ phenylalkyl, or $C_{11-20}$ naphthylalkyl;

$$\begin{array}{cccc} R_9 & Z_4 & O & R_{10} \\ | & | & \| & \diagup \\ -N-CH-C-N \\ & & & \diagdown \\ & & & R_{11}, \end{array} \quad (III)$$

wherein $Z_4$ is the identifying group of Gly, Ala, Val, Leu, Ile, Ser, Asp, Asn, Glu, $\beta$-Nal, Gln, Phe, X-Phe (where X is F, Cl, Br, $NO_2$, OH, or $CH_3$), $F_5$-Phe, Trp, Cys, Met, Pro, or HyPro; and each $R_9$, $R_{10}$, and $R_{11}$, independently, is H, $C_{1-20}$ alkyl, $C_{2-20}$ alkenyl, $C_{2-20}$ alkynyl, phenyl, naphthyl, $C_{7-20}$ phenylalkyl, or $C_{11-20}$ naphthylalkyl;

$$-N\begin{array}{c} R_{12} \\ \diagdown \\ \diagup \\ R_{13}, \end{array} \quad (IV)$$

wherein each $R_{12}$ and $R_{13}$, independently, is H, $C_{1-20}$ alkyl, $C_{2-20}$ alkenyl, $C_{2-20}$ alkynyl, phenyl, naphthyl, $C_{7-20}$ phenylalkyl, or $C_{11-20}$ naphthylalkyl;

provided that pGlu can only be a N-terminal residue and that when the N-terminal residue is pGlu, $R_1$ is H and $R_2$ is a bond linking the nitrogen of the $\alpha$-amino group and the carbon of the y-carboxyl group of pGlu; further provided that $A^1$ can be coupled with $Z_3$ through a disulfide bridge, where $A^1$ is Cys and $Z_3$ is the identifying group of Cys; and further provided that, for the groups (I) through (IV), any asymmetric carbon atom can be R, S or a racemic mixture.

Particularly preferred analogs covered by Formula (B) are those in which W is (I), or in which $A^0$ is Gly, D-Phe, or deleted;
$A^1$ is p-Glu, $F_5$-Phe, Aza-Tyr, D-Phe, D-Ala, D-$\beta$-Nal, D-Cpa, or D-Asn;
$A^2$ is Gln, His, 1-methyl-His, or 3-methyl-His;
$A^4$ is Ala;
$A^5$ is Val;
$A^6$ is Sar, Gly, D-Phe, or D-Ala;
$A^7$ is His, Lys(Z), Lys (COCH$_3$), Lys(COPh), Lys(COCH$_2$Ph), or Lys (COCH$_2$CH$_2$Ph); and,
W is (I), and $R_3$ is CH$_2$—CH$_2$, CH$_2$, or deleted and $Z_1$ is the identifying group of Leu or Phe; W is (I), and $R_3$ is CHOH—CH$_2$, $Z_1$ is the identifying group of Leu, Chx-Ala, or Phe and each $R_5$ and $R_6$, independently, is H; W is (I), and $V_1$ is NHR$_6$ in which $R_6$ is NH$_2$; W is (II), and $R_5$ is CH$_2$—NH and each $Z_2$ and $Z_3$, independently, is the identifying group of Leu or Phe; W is (III), and $Z_4$ is the identifying group of Leu, Phe, X-Phe (where X is F, Cl, Br, NO$_2$, OH, or CH$_3$) and each $R_9$, $R_{10}$ and $R_{11}$, independently, is H, $C_{1-20}$ alkyl, $C_{2-20}$ alkenyl, $C_{2-20}$ alkynyl, phenyl, naphthyl, $C_{7-20}$ phenylalkyl, or $C_{11-20}$ naphthylalkyl; or W is (IV), and each $R_{12}$ and $R_{13}$, independently, is H and each $R_1$ and $R_2$, independently, is H, $C_{1-20}$ alkyl, COE$_1$, or COOE$_1$. Preferably, (1) W is (I), and $R_3$ is CH$_2$—CH$_2$, CH$_2$, or deleted and $Z_1$ is the identifying group of Leu or Phe; (2) W is (I), and $R_3$ is CHOH—CH$_2$, $Z_1$ is the identifying group of Leu, Chx-Ala, or Phe, and each $R_5$ and $R_6$, independently, is H; (3) W is (I), and $V_1$ is NHR$_6$ in which $R_6$ is NH$_2$; (4) W is (II), and $R_5$ is CH$_2$—NH and each $Z_2$ and $Z_3$, independently, is the identifying group of Leu or Phe; (5) W is (III), and $Z_4$ is the identifying group of Leu, Phe, or X-Phe (where X is F, Cl, Br, NO$_2$, OH, or CH$_3$) and each $R_9$, $R_{10}$ and $R_{11}$, independently, is H, $C_{1-20}$ alkyl, $C_{2-20}$ alkenyl, $C_{2-20}$ alkynyl, phenyl, naphthyl, $C_{7-20}$ phenylalkyl, or $C_{11-20}$ naphthylalkyl; and (6) W is (IV), and each $R_{12}$ and $R_{13}$, independently, is H and each $R_1$ and $R_2$, independently, is H, $C_{1-20}$ alkyl, COE$_1$, or COOE$_1$.

Particularly preferred analogs are those in which W is (I), $R_3$ is CH$_2$—CH$_2$, CH$_2$, or deleted, $Z_1$ is the identifying group of Leu or Phe, $V_1$ is NHR$_6$ and $R_6$ is is H, $C_{1-20}$ alkyl, $C_{7-20}$ phenylalkyl, or $C_{1-20}$ acyl, e.g., D-Phe-Gln-Trp-Ala-Val-Gly-His-Leu-NH(C$_3$H$_7$).

It is also preferred that the bombesin analog of this invention have the following formula:

wherein
$A^1$ is D- or L-pGlu, or is deleted;
$A^2$ is Gln, Asn, Gly, Ala, Leu, Ile, Nle, $\alpha$-aminobutyric acid, Met, Val, Phe, p-X-Phe (where X is F, Cl, Br, OH or CH$_3$), Trp, $\beta$-naphthylalanine, or is deleted;
$A^3$ is D- or L-Arg, D- or L-Lys, or is deleted;
$A^4$ is Gln, Asn, Gly, Ala, Leu, Ile, Nle, $\alpha$-aminobutyric acid, Met, Val, Phe, p-X-Phe (where X is F, Cl, Br, OH or CH$_3$), Trp, $\beta$-naphtylalanine, or is deleted;
$A^5$ is a D- or L-amino acid selected from the group consisting of Gln, Asn, Gly, Ala, Leu, Ile, Nle, $\alpha$-aminobutyric acid, Met, Val, Phe, p-X-Phe (where X is F, Cl, Br, OH or CH$_3$), Trp, and $\beta$-naphthylalanine, or is deleted;
$A^6$ is a D- or L-amino acid selected from the group consisting of Gln, Asn, Gly, Ala, N-Ac-Ala, Leu, Ile, Nle, $\alpha$-aminobutyric acid, Met, Val, Phe, p-X-Phe (where X is F, Cl, Br, OH or CH$_3$), Trp, p-Glu, Sar, and $\beta$-naphthylalanine, or is deleted;
$A^7$ is Gln, Asn, Gly, Ala, Leu, Ile, Nle, $\alpha$-aminobutyric acid, Met, Val, D- or L-Phe, p-X-Phe (where X is F, Cl, Br, OH or CH$_3$), Trp, Lys, His, or $\beta$-naphthylalanine;
$A^8$ is Trp or Met;
$A^9$ is a D- or L-amino acid selected from the group consisting of Gln, Asn, Gly, Ala, Leu, Ile, Nle, $\alpha$-aminobutyric acid, Met, Val, Phe, p-X-Phe (where X is F, Cl, Br, OH or CH$_3$), Trp, and $\beta$-naphthylalanine;
$A^{10}$ is Gln, Asn, Gly, Ala, Leu, Ile, Nle, $\alpha$-aminobutyric acid, Met, Val, Phe, p-X-Phe (where X is F, Cl, Br, OH or CH$_3$), Trp, Thr, or $\beta$-naphthylalanine;
$A^{11}$ is a D- or L-amino acid selected from the group consisting of Gly, Ala and Phe;
$A^{12}$ is a D- or L-amino acid selected from the group consisting of His, Phe, and p-X-Phe (where X is F, Cl, Br, OH, CH$_3$);
$A^{13}$ is Gln, Asn, Gly, Ala, Leu, Ile, Nle, $\alpha$-aminobutyric acid, Met, Val, Phe, p-X-Phe (where X is F, Cl, Br, OH or CH$_3$), Trp, or $\beta$-naphthylalanine;
$A^{14}$ is Gln, Asn, Gly, Ala, Leu, Ile, Nle, $\alpha$-aminobutyric acid, Met, Val, Phe, p-X-Phe (where X is F, Cl, Br, OH or CH$_3$), Trp, or $\beta$-naphthylalanine;
each $R_1$, $R_2$, $R_3$ and $R_4$, independently, is H, $C_{1-20}$ alkyl, $C_{2-20}$ alkenyl, $C_{2-20}$ alkynyl, phenyl, naphthyl, $C_{7-20}$ phenylalkyl, $C_{11-20}$ naphthylalkyl, COE$_1$, or COOE$_1$ (where E$_1$ is $C_{1-20}$ alkyl, $C_{2-20}$ alkenyl, $C_{2-20}$ alkynyl, phenyl, naphthyl, $C_{7-20}$ phenylalkyl, $C_{11-20}$ naphthylalkyl, pyridyl, or indolyl); provided that when either $R_1$ or $R_2$ is COE$_1$ or COOE$_1$, the other must be H and when either $R_3$ or $R_4$ is COE$_1$ or COOE$_1$, the other must be H; further provided that pGlu can only be a N-terminal residue and that when the N-terminal residue is pGlu, $R_1$ is H and $R_2$ is a bond linking the nitrogen of the $\alpha$-amino group and the carbon of the $\gamma$-carboxyl group of pGlu; further provided that for each of the residues $A^7$, $A^8$, $A^9$, $A^{11}$, $A^{12}$, and $A^{13}$, independently, the carbon atom participating in the amide bond between that residue and the nitrogen atom of the $\alpha$-amino group of the adjacent amino acid residue may be a carbonyl carbon or may be reduced to a methylene carbon.

Particularly preferred analogs covered by Formula (C) are those in which $A^1$ through $A^6$ are deleted, $A^{13}$ is Leu, $A^{14}$ is Leu, and the carbon atom participating in the amide bond between $A^3$ and $A^{14}$ is a methylene carbon.

Note that unless otherwise specified, the symbols $A^1$, $A^2$, or the like herein stands for an amino acid residue, i.e., —NH—CH(R)—CO— or =N—CH(R)—CO— when it is at the N-terminus and —NH—CH(R)—CO— when it is not at the N-terminus, where R denotes the identifying group (i.e., side chain) of an amino acid or its residue, e.g., R is $CH_2COOH$ for Asp. Also, where the amino acid residue is optically active, it is the L-form configuration that is intended unless D-form is expressly designated. $COE_1$ stands for and $COOE_1$ for HyPro herein refers to any of 2-hydroxy-Pro, 3-hydroxy-Pro, 4-hydroxy-Pro, and 5-hydroxy-Pro; 4-hydroxy-Pro is preferred.

Other features and advantages of the present invention will be apparent from the following description of the preferred embodiments thereof, as well as from the claims.

DESCRIPTION OF THE PREFERRED EMBODIMENTS

Figure 1A:
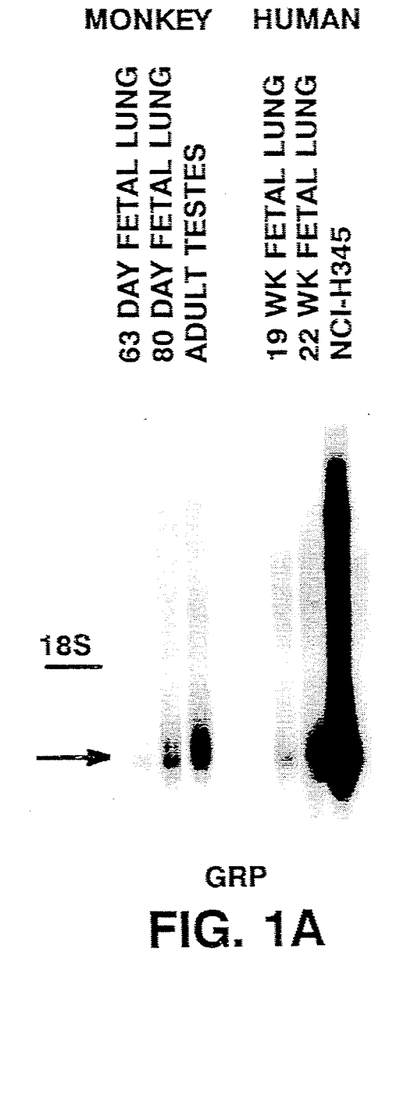
FIGS. 1A and 1B are results from Northern blot analysis of GRP mRNA (FIG. 1A) and GRP-receptor mRNA (FIG. 1B) in monkey and human tissues.

High levels of mRNA that hybridizes to the human GRP cDNA were found to be present in monkey testes. Northern blot analysis clearly shows that GRP mRNA present in monkey testes in higher concentrations than in non-neoplastic tissue such as lung (FIG. 1A). In addition, in situ hybridization has clearly localized the GRP mRNA to developing sperm. Also shown as controls in FIG. 1A are results from Northern blotting of GRP mRNA in human fetal lung and in NCI-H345 cells, which is a human small cell lung carcinoma cell line. Both human fetal lung and NCI-H345 are known to express high levels of GRP.

Sequence analysis of partial cDNA clones (which lacked the 5'-end of the mRNA and the coding region for the bombesin-like peptide) derived from a monkey testes cDNA library shows that the hybridizing mRNA is clearly related to human GRP. Furthermore, hybridization study suggests that the 5'-end of this mRNA may be different and could thus encode a new bombesin-like peptide (i.e., other than GRP), or alternately may encode the monkey homolog of GRP.

Figure 1B:
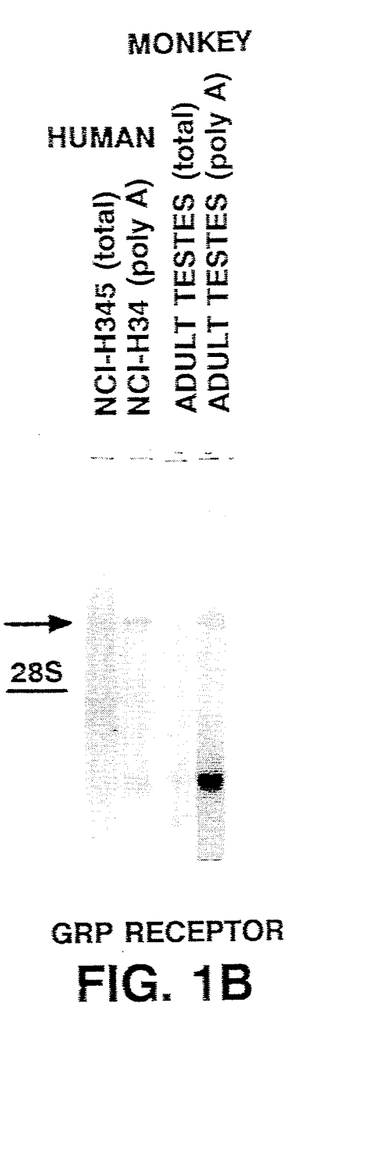

As shown in Figure 1B, Northern blot analysis reveals the presence of the GRP receptor (i.e., receptor for a bombesin-like peptide such as GRP) mRNA in monkey testes. Results from control experiments using NCI-H345 cells are also shown. Sequence analysis of a cDNA clone derived from a monkey testes cDNA library shows strong homology with the human GRP receptor that has been characterized in small cell lung carcinoma.

A new GRP receptor, which is expressed in very high levels in rat sperm, has recently been cloned. cDNA encoding this receptor was used to determine if this new GRP receptor is expressed in primate sperm. The results show that this receptor is not expressed in primate sperm. In addition, in transfected cells and Xenopus oocytes, the new receptor reacted only weakly to GRP and Neuromedin B. However, the responses that were present were clearly blocked by GRP receptor antagonists, such as BIM 26147.

The above-discussed data and experimental results to be presented below suggest that a bombesin-like peptide is an endogenous component of normal fertilization of the oocyte by sperm. Thus, bombesin analogs can be used either as contraceptive agents (e.g., added to contraceptive foam, jelly or condoms) or as fertilization agents (e.g., aiding in vitro fertilization and artificial insemination procedures).

Synthesis of Bombesin Analogs

The synthesis of the bombesin analog pGlu-Gln-TrP-Ala-Val-Gly-His-Leu-ψ[$CH_2NH$]-Leu-$NH_2$ (SEQ ID NO: 3) follows. Other bombesin analogs were prepared by making appropriate modifications of the following synthetic method.

The first step was the preparation of the intermediate, pGlu-Gln-Trp-Ala-Val-Gly-His (benzyloxycarbonyl)-Leu-ψ[$CH_2NH$]-Leu-benzhydrylamine resin, as follows.

Benzhydrylamine-polystyrene resin (Vega Biochemicals, Inc.) (0.97 g, 0.5 mmole) in the chloride ion form was placed in the reaction vessel of a Beckman 990B peptide synthesizer programmed to perform the following reaction cycle: (a) methylene chloride; (b) 33% trifluoroacetic acid (TFA) in methylene chloride (2 times for 1 and 25 min. each); (c) methylene chloride; (d) ethanol; (e) methylene chloride; and (f) 10% triethylamine in chloroform.

The neutralized resin was stirred with α-t-butoxycarbonyl("BOC")-Leu and diisopropylcarbodiimide (1.5 mmole each) in methylene chloride for 1 hour, and the resulting amino acid resin was then cycled through steps (a) to (f) in the above wash program. BOC-Leu aldehyde (1.25 mmoles), prepared by the method of Fehrentz and Castro, Synthesis, p. 676 (1983), was dissolved in 5 ml of dry dimethylformamide (DMF) and added to the resin TFA salt suspension followed by the addition of 100 mg (2 mmoles) of sodium cyanoborohydride [Sasaki and Coy, Peptides 8:119–121 (1987); Coy et al., Id.]. After stirring for 1 hour, the resin mixture was found to be negative to ninhydrin reaction (1 min.), indicating complete derivatization of the free amino group.

The following amino acids (1.5 mmole) were then coupled successively in the presence of diisopropyl-carbodiimide (1.5 mmole), and the resulting amino acid resin was cycled through washing/deblocking steps (a) to (f) in the same procedure as above: BOC-His(benzyloxycarbonyl), BOC-Gly (coupled as a 6M excess of the p-nitro-phenylester), BOC-Val, BOC-Ala, BOC-Trp, BOC-Gln (coupled as a 6M excess of the p-nitrophenylester), and pGlu. The completed resin was then washed with methanol and air dried.

The resin described above (1.6 g, 0.5 mmole) was mixed with anisole (5 ml) and anhydrous hydrogen fluoride (35 ml) at 0° C. and stirred for 45 min. Excess hydrogen fluoride was evaporated rapidly under a stream of dry nitrogen, and free peptide was precipitated and washed with ether. The crude peptide was dissolved in a minimum volume of 2M acetic acid and eluted on a column (2.5×100 mm) of Sephadex G-25 (Pharmacia Fine Chemicals, Inc.). Fractions containing a major component by UV absorption and thin layer chromatography ("TLC") were then pooled, evaporated to a small volume and applied to a column (2.5×50 cm) of octadecylsilane-silica (Whatman LRP-1, 15-20 μm mesh size).

The peptide was eluted with a linear gradient of 0-30% acetonitrile in 0.1% trifluoroacetic acid in water. Fractions were examined by TLC and analytical high performance liquid chromatography ("HPLC") and pooled to give maximum purity. Repeated lyophilization of the solution from water gives 60 mg of the product as a white, fluffy powder.

The product was found to be homogeneous by HPLC and TLC. Amino acid analysis of an acid hydrolysate confirms the composition of the peptide. The presence of the Leu-ψ[ψ CH₂—NH]-Leu bond was demonstrated by fast atom bombardment mass spectrometry. pGlu-Gln-Trp-Ala-Val-Gly-His-Phe-ψ[CH₂NH]-Leu-NH₂(SEQ ID NO: 4), pGlu-Gln-Arg-Leu-Gly-Asn-Gln-Trp-Ala-Val-Gly-D-Phe-Leu-Met-NH₂, pGlu-Gln-Arg-Leu-Gly-Asn-Gln-Trp-Ala-Val-Gly-D-Phe-Leu-Met-NH₂, or other peptides were prepared in similar yields in an analogous fashion by appropriately modifying the above procedure.

Solid phase synthesis of D-Phe-Gln-Trp-Ala-Val-Gly-His-Leu-ψ[CH₂NH]-D-Phe-NH₂, was carried out as follows:

BOC-D-Phe-Gln-Trp-Ala-Val-Gly-His(tosyl)-Leu-ψ[CH₂NH]-D-Phe-benzhydrylamine resin was synthesized first.

Benzhydrylamine-polystyrene resin (Advanced ChemTech, Inc.) (1.25 g, 0.5 mmole) in the chloride ion form was placed in the reaction vessel of an Advanced ChemTech ACT 200 peptide synthesizer programmed to perform the following reaction cycle: (a) methylene chloride; (b) 33% trifluoroacetic acid in methylene chloride (2 times for 1 and 25 min. each); (c) methylene chloride; (d) ethanol; (e) methylene chloride; (f) 10% triethylamine in chloroform.

The neutralized resin was stirred with BOC-D-phenylalanine and diisopropylcarbodiimide (1.5 mmole each) in methylene chloride for 1 hour and the resulting amino acid resin was then cycled through steps (a) to (g) in the above wash program. The BOC group was then removed by TFA treatment. BOC-Leu aldehyde (1.25 mmoles), prepared by the method of Fehrentz and Castro, Id., was dissolved in 5 ml of dry DMF and added to the resin TFA salt suspension followed by the addition of 100 mg (2 mmoles) of sodium cyanoborohydride. After stirring for 1 hour, the resin mixture was found to be negative to ninhydrin reaction (1 min.) indicating complete derivatization of the free amino group.

The following amino acids (1.5 mmole) were then coupled successively by the same procedure: BOC-His(benzyloxycarbonyl), BOC-Gly, BOC-Val, BOC-Ala, BOC-Trp, BOC-Gln (coupled in the presence of 1 equiv. hydroxybenzotriazole), BOC-D-Phe (coupled in the presence of 1 equiv. hydroxybenzotriazole). After drying, the peptide resin weighed 1.93 g.

The resin (1.93 g, 0.5 mmole) was mixed with anisole (5 ml) and anhydrous hydrogen fluoride (35 ml) at 0° C. and stirred for 45 min. Excess hydrogen fluoride was evaporated rapidly under a stream of dry nitrogen and free peptide precipitated and washed with ether. The crude peptide was dissolved in a minimum volume of 2M acetic acid and eluted on a column (2.5×100 mm) of Sephadex G-25. Fractions containing a major component by UV absorption and TLC were then pooled, evaporated to a small volume and applied to a column (2.5×50 cm) of Vydac octadecylsilane (10-15 uM). This was eluted with a linear gradient of 15-45% acetonitrile in 0.1% trifluoroacetic acid in water. Fractions were examined by TLC and analytical HPLC and pooled to give maximum purity. Repeated lyophilization of the solution from water gives 120 mg of the product as a white, fluffy powder.

The product was found to be homogeneous by HPLC and TLC. Amino acid analysis of an acid hydrolysate confirms the composition of the peptide. The presence of the Leu-ψ[CH₂NH]peptide bond was demonstrated by fast atom bombardment mass spectrometry.

The analog D-Cpa-Gln-Trp-Ala-Val-Gly-His-Leu-ψ[CH₂NH]-Phe-NH₂ (BIM 26159) may be synthesized in a similar manner by substituting D-Cpa for D-Phe.

Solid phase synthesis of [D-Phe¹, His⁷, desMet⁹] Litorin, D-Phe-Gln-Trp-Ala-Val-Gly-His-Leu-NH₂, was carried out as follows:

Step (1): Benzhydrylamine-polystyrene resin (Advanced ChemTech, Inc. (0.62 gm, 0.25 mmole) in the chloride ion form was placed in the reaction vessel of an ACT 200 peptide synthesizer programmed to perform the following reaction cycle: (a) methylene chloride; (b) 33% trifluoroacetic acid in methylene chloride (2 times for 1 and 25 min. each); (c) methylene chloride; (d) ethanol; (e) methylene chloride; (f) 10% triethylamine in chloroform.

The neutralized resin was stirred with BOC-Leu and diisopropylcarbodiimide (1.5 mmole each) in methylene chloride for 1 hour and the resulting amino acid resin was then cycled through steps (a) to (f) in the above wash program. The following amino acids (1.5 mmole) were then coupled successively by the same procedure: BOC-His(benzyloxycarbonyl), BOC-Gly, BOC-Val, BOC-Ala, BOC-Trp, BOC-Gln (coupled as a 6M excess of the p-nitrophenylester, and BOC-D-Phe (coupled in the presence of hydroxybenzotriazole). After drying, the peptide resin weighed 0.92 g.

Step (2): The resin (0.92 g) was then mixed with anisole (5 ml), dithiothreitol (200 mg) and anhydrous hydrogen fluoride (35 ml) at 0° C. and stirred for 45 min. Excess hydrogen fluoride was evaporated rapidly under a stream of dry nitrogen and free peptide precipitated and washed with ether. The crude peptide was dissolved in a minimum volume of 2M acetic acid and eluted on a column (2.5×100 cm) of Sephadex G-25. Fractions containing a major component by UV absorption and TLC were then pooled, evaporated to a small volume and applied to a column (2.5×50 cm) of Vydac octadecylsilane (10-15 micron). The column was eluted with a linear gradient of 0-3.0% acetonitrile in 0.1% trifluoroacetic acid in water. Fractions were examined by TLC and pooled to give maximum purity. Repeated lyophilization of the solution from water gives a white, fluffy powder; this product was found to be homogeneous by HPLC and TLC. Amino acid analysis of an acid hydrolysate confirms the composition of the peptide.

Synthesis of D-β-Nal-Gln-Trp-Ala-Val-Gly-His-Leu-NH$_2$ was accomplished using the same procedure as described above.

Synthesis of N-acetyl-D-Phe-Gln-Trp-Ala-Val-Gly-His-Leu-NH$_2$ was accomplished using the same procedure as that described above, except that the final BOC group was removed and the resin acetylated with acetic anhydride in methylene chloride.

The synthesis of [Sta$^8$, desMet$^9$] Litorin follows. Sta is an abbreviation of statin or (3S, 4S)-4-amino-3-hydroxy-6-methylheptanoic acid. A statin, AHPPA [i.e., (3S,4S)-4-amino-3-hydroxy-5-phenylpentanoic acid], or ACHPA [i.e., (3S, 4S)-4-amino-5-cyclohexyl-3-hydroxypentanoic acid] residue was substituted in place of any two amino acids of the analog, where the peptide contains only peptide bonds. For example, [Sta$^8$, desMet$^9$] Litorin was prepared in an analogous fashion by first coupling statin to the resin and then proceeding with the addition of BOC-His(benzylocarbonyl).

Statine or BOC-statine was synthesized according to the method of Rich et al., 1978, J. Organic Chem. 43; 3624; and Rich et al., 1980, J. Med. Chem. 23: 27, and AHPPA and ACHPA were synthesized according to the method of Hui et al., 1987, J. Med. Chem. 30: 1287; Schuda et al., 1988, J. Org. Chem. 53:873; and Rich et al., 1988, J. Org. Chem. 53:869.

Solid-phase synthesis of the peptide pGlu-Gln-Trp-Ala-Val-Gly-His-Sta-NH$_2$ was accomplished through the use of the following procedures in which BOC-statine (prepared by the procedure of Rich et al., J. Org. Chem. 1978, 43, 3624) was first coupled to methyl-benzhydrylamine-polystyrene resin. After acetylation, the intermediate p-Glu-Gln-Gln-Trp-Ala-Val-Gly-His(benzyloxycarbonyl)-Sta-methylbenzhydrylamine resin was prepared. The synthetic procedure used for this preparation follows in detail:

1. Incorporation of BOC-statine on methylbenzhydrylamine resin.

Methylbenzhydrylamine-polystyrene resin (Vega Biochemicals, Inc.) (1.0 g, 0.73 mmol) in the chloride ion form was placed in the reaction vessel of a Vega 250C Coupler peptide synthesizer. The synthesizer was programmed to perform the following reactions: (a) methylene chloride; (b) 10% triethylamine in chloroform; (c) methylene chloride; and (d) dimethylformamide.

The neutralized resin was mixed for 18 hours with the preformed active ester made from BOC-statine (1.46 mmol), diisopropyl carbodiimide (2 mmol), and hydroxybenzotriazole hydrate (1.46 mmol in dimethylformamide at 0° C. for one hour. The resulting amino acid resin was washed on the synthesizer with dimethylformamide and then methylene chloride. The resin mixture at this point was found by the Kaiser ninhydrin test (5 min.) to have an 84% level of statine incorporation on the resin.

Acetylation was performed by mixing the amino acid-resin for 15 min. with N-acetyl imidazole (5 mmol) in methylene chloride. Derivatization to the 94–99% level of the free amino groups of the resin was indicated by the Kaiser ninhydrin test (5 min.). The BOC-statine-resin was then washed with methylene chloride.

2. Couplings of the Remaining Amino Acids.

The peptide synthesizer was programmed to perform the following reaction cycle: (a) methylene chloride; (b) 33% trifluoroacetic acid (TFA) in methylene chloride (2 times for 5 and 25 min. each); (c) methylene chloride; (d) isopropyl alcohol; (e) 10% triethylamine in chloroform; and (f) ethylene chloride.

The following amino acids (2.19 mmol) were then coupled successively by diisopropyl carbodiimide (4 mmol) alone or diisopropyl carbodiimide (4 mmol) plus hydroxybenzotriazole hydrate (1.47 or 0.73 mmol) and the resulting peptide-resin was washed on the synthesizer with dimethylformamide and then methylene chloride, and then cycled through the washing and deblocking steps (a) to (f) in the procedure described above.

BOC-His (benzyloxycarbonyl) (coupled in the presence of 2 equivalents hydroxybenzotriazole); BOC-Gly; BOC-Val; BOC-Ala and BOC-Trp (coupled as the preformed hydroxybenzotriazole active esters made by reaction at 0° C. for one hour with 1 equivalent hydroxybenzotriazole hydrate); BOC-Gln and pGlu (also coupled as the preformed active esters of hydroxybenzotriazole made by reaction at 0° C. for one hour with 1 equivalent hydroxybenzotriazole hydrate). The completed peptide-resin was then washed with methanol and air dried.

The peptide-resin described above (1.60 g, 0.73 mmol) was mixed with anisole (2.5 ml), dithioerythreitol (50 mg), and anhydrous hydrogen fluoride (30 ml) at 0° C. for one hour. Excess hydrogen fluoride was evaporated rapidly under a stream of dry nitrogen, and the free peptide was precipitated and washed with ether. The crude peptide was dissolved in 100 mL of 1M acetic acid and the solution was then evaporated under reduced pressure. The crude peptide was dissolved in a minimum volume of methanol/water 1/1 and triturated with 16 volumes of ethyl acetate.

The triturated peptide was applied to a column (9.4 mm I.D.×50 cm) of octadecylsilane-silica (Whatman Partisil 10 ODS-2 M9). The peptide was eluted with a linear gradient of 20–80% of 20/80 0.1% trifluoroacetic acid/acetonitrile in 0.1% trifluoroacetic acid in water. Fractions were examined by TLC and analytical HPLC and pooled to give maximum purity. Lyophilization of the solution from water gives 77 mg of the product as a white fluffy powder.

The synthesis of the bombesin analog, D-Phe-Gln-Trp-Ala-Val-Gly-His-Leu-Leu-NH$_2$ (BIM 26187), follows. Other similar bombesin analogs were prepared by making appropriate modifications of the following synthetic method.

1) Incorporation of BOC-Leu on 4-methyl benzhydrylamine.

4-methyl benzhydrylamine-polystyrene resin (Bachem, Inc.) (0.72 meq/g) in the chloride ion form was placed in the reaction vessel of an ACT200 peptide synthesizer (Advanced Chem Tech, Inc.) programmed to perform the following reaction cycle: (a) methylene chloride; (b) 10% triethylamine in chloroform; (c) methylene chloride; and (d) dimethylformide.

The neutralized resin was mixed with BOC-Leu and diisopropylcarbodiimide (3 molar eq. each) in methylene chloride for 1 hour. The resulting amino acid resin was washed on the synthesizer with dimethyl-formamide and treated with 5% acetic anhydride in dimethylformamide for 5 min. Then it was washed with dimethylformamide and methylene chloride.

2) Couplings of the remaining amino acids.

The peptide synthesizer was programmed to perform the following reaction cycle: (a) methylene chloride; (b) 33% trifluoroacetic acid (TFA) in methylene chloride (2 times for 5 and 25 min. each); (c) methylene chloride;

(d) isopropyl alcohol; (e) 10% triethylamine in chloroform; and (f) methylene chloride.

The following amino acids (3 molar eq.) were then coupled successively by the same procedure: BOC-Leu, BOC-His (tosyl), BOC-Gly, BOC-Val, BOC-Ala, BOC-Trp, BOC-Gln (coupled in the presence of 1 eq. hydroxybenzotriazole), BOC-D-Phe (coupled in the presence of 1 eq. hydroxybenzotriazole). The completed resin was then washed with methanol and air dried.

The peptide resin described above (1.41 g) was mixed with anisole (5 ml), dithioerythreitol (50 mg), and anhydrous hydrogen fluoride (25 ml) at 0° C. for one hour. Excess hydrogen fluoride was evaporated rapidly under a stream of dry nitrogen, and the residue was washed in ether. Crude peptide was dissolved in 100 ml of 4M acetic acid and the solution was then evaporated under reduced pressure. The crude peptide was dissolved in minimum volume of methanol/water and triturated with ethyl acetate. The triturated peptide was applied to a column (9.4 mm I.D.×50 cm) of octadecylcilane-silica (Whatman Partisil 10 ODS-2M9). The peptide was eluted with a linear gradient of 20-80% of 50/50 0.1% TFA/acetonitrile in 0.1% TFA in water. Fractions were examined by analytical HPLC and appropriate fractions were evaporated to a small volume, which was further lyophilized, gives 65 mg of the product as a colorless powder.

Other compounds including [D-Cpa$^1$, β-Leu$^8$, desMet$^9$] Litorin, or compounds containing, e g., ChxAla$^8$ or Nle$^9$, were prepared as above; a statine, AHPPA, ACHPA, β-amino acid, or γ-amino acid residue was added in the same way as was a natural α-amino acid residue, by coupling as a BOC derivative.

Resins used for peptide synthesis were selected according to the chemical structure of the C-terminus of the peptide. More specifically, Merrifield resin was coupled to the first amino acid by an ester bond which, upon cleavage, yielded a carboxyl C-terminus; methylbenzhydrylamine and benzylhydrylamine resins, on the other hand, were coupled to the first amino acid by a secondary amine bond which, upon cleavage, yielded an amide C-terminus.

Peptides modified at their C-terminal end were prepared by appropriate modifications of the procedure described above. For example, 0-methyl ester derivatives was synthesized as described in Camble et al., "ICI 216140 A Potent In Vivo Antagonist Analogue of Bombesin/Gastrin Releasing Peptide Derived From the C-Terminal Sequence Lacking the Final Methionine Residue", Life Science, Oct.-Nov. 1989, hereby incorporated by reference.

Camble et al. describe the synthesis of an analog of bombesin having a trimethylacetyl-modified N-terminus and a methyl-ester modified C-terminus. This analog, (CH$_3$)$_3$C—CO-His-Trp-Ala-Val-D-Ala-His-Leu-OCH$_3$, was synthesized by solid phase methods, as described above. The N-terminal trimethylacetyl modification can be obtained by reaction of the corresponding anhydrides with the peptide. The C-terminal methyl ester modification can be obtained by treating the peptide resin with methanol and triethylamine.

We describe below how a peptide analog with a substituted amide C-terminus can be prepared. Synthesis of BIM 26147 is used as an example.

First, Leu-O-polystyrene Merrifield resin (1.5 g, 0.5 mmole) was placed in the reaction vessel of an Advanced ChemTech ACT 200 peptide synthesizer programmed to perform the following wash/reaction cycle (2 times for 1 and 25 min each); (c) methylene chloride; (d) ethanol; (e) methylene chloride; (f) 10% triethylamine in chloroform. The neutralized resin was stirred with Boc-Leu and diisopropylcarbodiimide (1.5 mmole each) in methylene chloride for 1 hr and the resulting amino acid resin was then cycled through steps (a) to (f) in the above program.

The following amino acids (1.5 mmole) were then coupled successively by the same procedure: Boc-His (N-im-Boc), Boc-Gly, Boc-Val, Boc-Ala, Boc-Trp, Boc-Gln (coupled in the presence of 1 equiv. hydroxybenzotriazole), Boc-D-Phe (coupled in the presence of 1 equiv. hydroxybenzotriazole). The final Boc group was then removed by 33% trifluoracetic acid treatment. After drying, the peptide resin weighed 1.9 g.

The resin thus obtained (1.9 g, 0.5 mmole) was suspended in 25% propylamine/DMF and stirred (24 hr). After removal of the volatile components, the crude peptide was dissolved in a minimum volume of 2M acetic acid and eluted on a column (2,5×100 mm) of Sephadex G-25. Fractions containing a major component by UV absorption and TLC were then pooled, evaporated to a small volume and applied to a column (1.5×50 cm) of Vydac octadecylsilane (10–15 uM), followed by elution with a linear gradient of 15–45% acetonitrile in 0.1% trifluoroacetic acid in water. Fractions were examined by TLC and analytical HPLC and pooled to give maximum purity. Repeated lyophilization of the solution from water gave 220 mg of the product as a white, fluffy powder. The product was found to be homogeneous by HPLC and TLC. Amino acid analysis of an acid hydrolysate confirmed the composition of the octapeptide. The structure of the product was further confirmed by fast atom bombardment mass spectrometry.

Peptides of the invention may be cyclized by formation of disulfide bridges if there are two cysteine residues present in the peptide.

Effect of Bombesin Analogs on Acrosome Reaction

I. Bombesin and GRP stimulate the spontaneous acrosome reaction in both monkeys (rhesus) and humans.

The acrosome reaction, which is necessary for sperm to fertilize the egg, was induced by the following methods.

For monkeys, sperm was collected, washed twice in balanced salts, resuspended in lactate/bicarbonate and dibutyryl cAMP, and then incubated for 60 minutes. These are the conditions which have been demonstrated to capacitate sperm for monkey in vitro fertilization. See Wolf, D. P. et al. Mol. Reprod. Dev. 27:261–280 (1990); Lanzendorf, S. E. et al. Mol. Reprod. Dev. 25:61–66 (1990); and Wolf D. P. et al. Biol. Reprod. 41:335–346 (1989). All of these three publications are hereby incorporated by reference.

To measure the effects of bombesin on the acrosome reaction, capacitation was conducted in the presence or absence of bombesin. After incubation, samples of sperm were removed to determine the percentage of sperm which had undergone the acrosome reaction as measured with an acrosome specific monoclonal antibody and FITC fluorescence [see Wolf, D. P. Am. J. Reprod. Immunol. 20:106–113 (1989), which is hereby incorporated by reference].

For human sperm, capacitation was achieved by overnight incubation of sperm in balanced salt and 0.3% bovine serum albumin, after which bombesin was added to induce the acrosome reaction.

Figure 2:
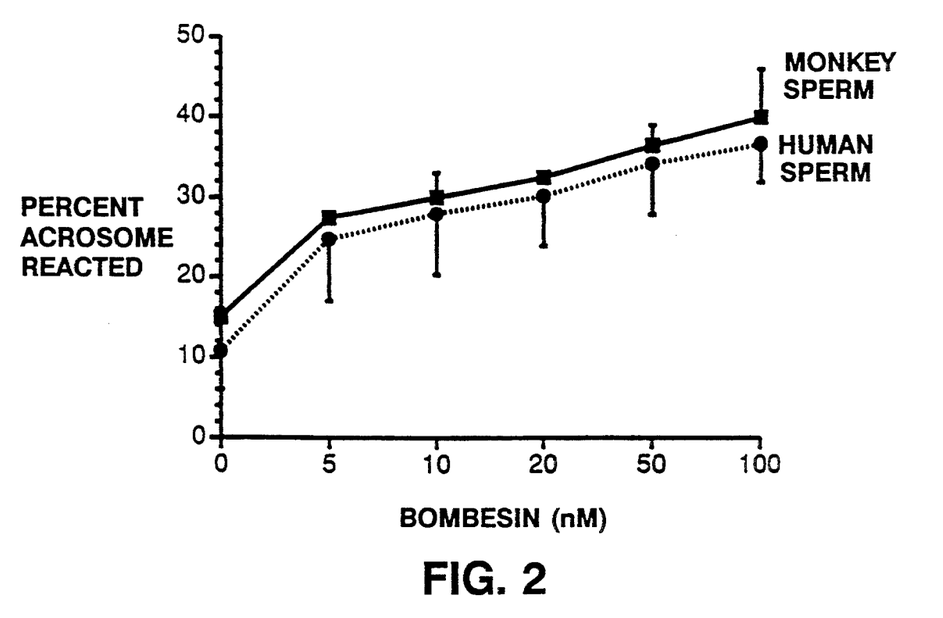
FIG. 2 is a graph showing effect of bombesin on induction of acrosome reaction.

As shown in FIG. 2, concentrations as low as 5 nM bombesin caused a 2-fold increase in the acrosome reaction in both monkey and human sperm. The bombesin-induced stimulation of the acrosome reaction could be blocked by the bombesin analog BIM 26147 (See FIG. 3).

Figure 3A:
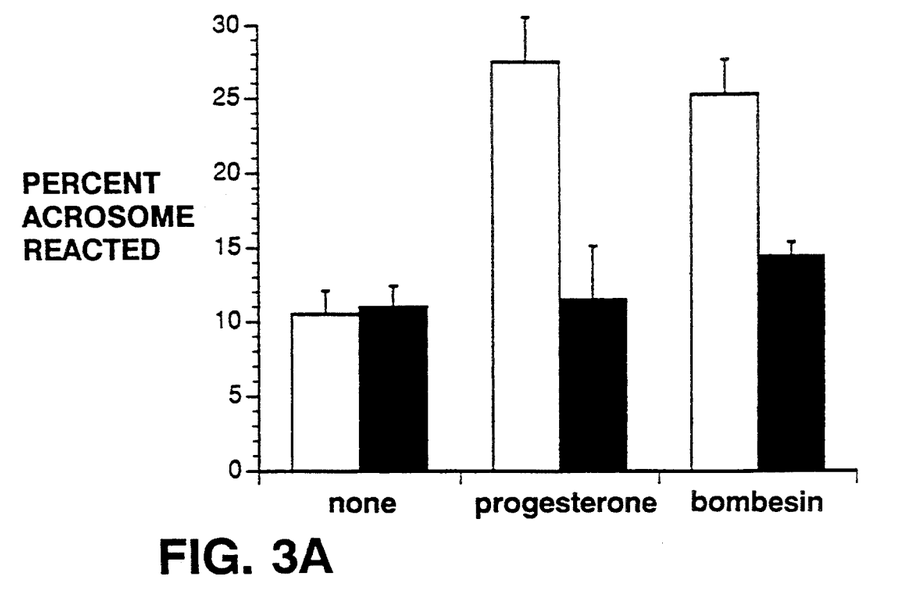
FIG. 3 is a graph showing effect of the bombesin analog D-Phe-Gln-Trp-Ala-Val-Gly-His-Leu-$NH(C_3H_7)$ (code name: BIM 26147) on bombesin or progesterone induced acrosome reaction in human and monkey sperm. Closed and open bars stand for use of BIM 26147 and blank control, respectively.
Figure 3B:
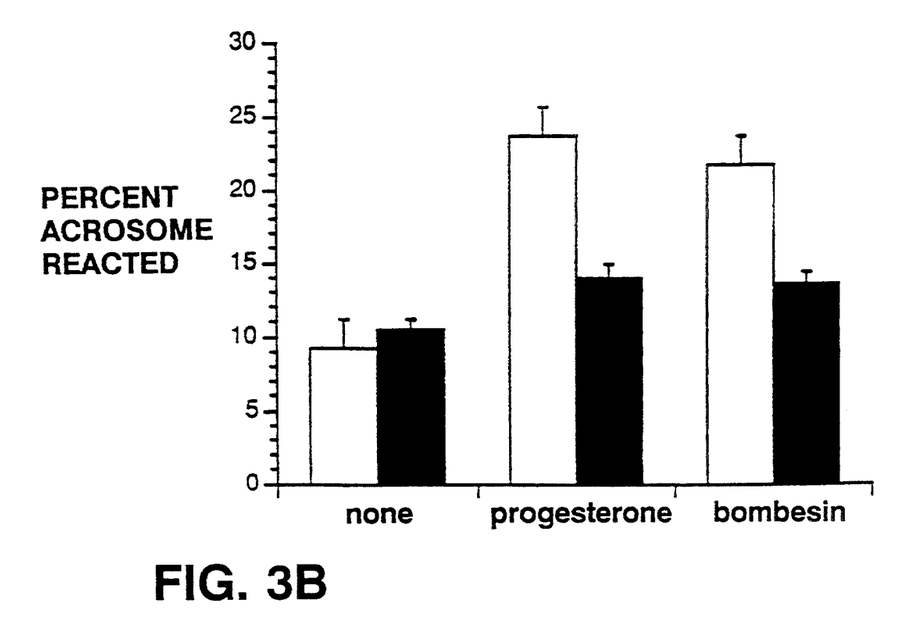

High doses of progesterone (1 μg/ml) acting through an as yet unknown mechanism also induce the acrosome reaction. Thomas, P. et al. Influx. Biochem. J. 264:539–546 (1989); Blackmore, P. F., et al. J. Biol. Chem. 265:1376–1380 (1990). As also shown in FIG. 3, the progesterone induced acrosome reaction could also be blocked by BIM 26147.

Human GRP, like bombesin, was also found to be a potent peptide capable of stimulating the acrosome reaction, i.e., it is active at 1 nM.

II. Effect of Various Bombesin Analogs on the Acrosome Reaction

Eight bombesin analogs, BIM 26136, BIM 26187, BIM 26189, BIM 26224, BIM 26226, BIM 26244, and BIM 26028, were used to test their effect on the acrosome reaction, either alone or in the presence GRP, in a manner described above.

The structures of the analogs tested are as follows:

BIM 26136: H-D-Nal-Gln-Trp-Ala-Val-Gly-His-Leu-ψ(CH$_2$-NH)-Phe-NH$_2$

BIM 26187: H-D-Phe-Gln-Trp-Ala-Val-Gly-His-Leu-Leu-NH$_2$

BIM 26189: H-D-Phe-Gln-Trp-Ala-Val-Gly-His-Leu-Cpa-NH$_2$

BIM 26224: H-D-Phe-Gln-Trp-Ala-Val-Gly-His-Phe-Nle-NH$_2$

BIM 26226: H-D-F$_5$-Phe-Gln-Trp-Ala-Val-D-Ala-His-Leu-OCH$_3$

BIM 26244: H-Propionyl-His-Trp-Ala-Val-D-Ala-His-Leu-OCH$_3$

BIM 26028: H-pGlu-Gln-Arg-Leu-Gly-Asn-Gln-Trp-Ala-Val-Gly-His-Leu-ψ(CH$_2$-NH)-Leu-NH$_2$ (SEQ ID NO: 5)

TABLE 1

EFFECT OF VARIOUS ANALOGS ON THE ACROSOME REACTION IN THE PRESENCE OR ABSENCE OF GRP (% Acrosome Reacted)

| | Analog* | Analog* + GRP# |
|---|---|---|
| Blank control | 6.000 ± .707 | 18.000 ± 3.629 |
| BIM 26136 | 11.000 ± .408 | 10.000 ± 1.225 |
| BIM 26137 | 7.000 ± .707 | 7.000 ± .707 |
| BIM 26169 | 10.000 ± .913 | 6.000 ± .408 |
| BIM 26224 | 9.000 ± 1.581 | 6.000 ± 1.000 |
| BIM 26226 | 9.000 ± 1.780 | 12.000 ± .707 |
| BIM 26244 | 5.000 ± .707 | 11.000 ± .677 |
| BIM 26028 | 8.000 ± .913 | 8.000 ± .707 |

*Final concentration: 50 nM
Final concentration: 2 nM

As shown in Table 1 above, among the seven analogs tested, BIM 26136 is the most potent in inducing the acrosome reaction.

III. Bombesin analog BIM 26147 blocks the in vitro fertilization of the monkey egg by monkey sperm.

As discussed above, while bombesin and some analogs thereof stimulate the acrosome reaction, other bombesin analogs block the acrosome reaction which is induced either by bombesin or by natural products such as progesterone. For example, BIM 26147 completely blocks progesterone and bombesin induced stimulation of the acrosome reaction.

Since the acrosome reaction is necessary for successful fertilization, we predicted that some bombesin analogs should be able to block fertilization. The prediction was confirmed by blocking in vitro fertilization of rhesus monkey ova by sperm by adding BIM 26147 to the fertilization reaction.

More specifically, the standard in vitro fertilization protocol was followed [see Wolf, D. P. et al. Mol. Reprod. Dev. 27:261–280 (1990) and Lanzendorf, S. E. et al. Mol. Reprod. Dev. 25:61–66 (1990), hereby incorporated by reference], with the exception that 100 nM BIM 26147 was added to the capacitation and fertilization reactions for some of the eggs. Two independent experiments were conducted. In the first experiment, 1 of 5 BIM 26147-treated eggs were fertilized versus 3 of 6 control eggs; in the second experiment, 0 of 4 BIM 26147-treated eggs were fertilized versus 12 of 20 control eggs.

The methods set forth above are well-known in the art. Thus, it is within the ability of a skilled artisan to use such methods in screening compounds for bombesin analogs capable of promoting and blocking fertilization, respectively.

Other Embodiments

The foregoing description has been limited to specific embodiments of this invention. It will be apparent, however, that variations and modifications may be made to the invention, with the attainment of some or all of the advantages of the invention. Such embodiments are also within the scope of the following claims.

What is claimed is:

1. A method of promoting fertilization by stimulating the acrosome reaction, said method comprising the step of contacting sperm either at the time of sperm capacitation or at the time of egg fertilization with an effective amount of bombesin or its agonist.

2. The method of claim 1 as applied to in vitro fertilization or artificial insemination for promoting fertilization.

3. The method of claim 1 in which said bombesin or its agonist is administered vaginally to a female subject for promoting fertilization.

4. The method of claim 1 in which said bombesin or its agonist is administered systemically or locally to a male subject for promoting fertilization.

5. The method of claim 4 in which said bombesin or its agonist is administered locally.

6. The method of claim 5 in which said bombesin or its agonist is administered by implantation of a biodegradable or retrievable polymer formulation in the scrotum.

7. The method of claim 1 in which said bombesin or its agonist is bombesin or GRP.

8. The method of claim 2 in which said bombesin or its agonist is bombesin or GRP.

9. The method of claim 3 in which said bombesin or its agonist is bombesin or GRP.

10. The method of claim 4 in which said bombesin or its agonist is bombesin or GRP.

11. A method of blocking fertilization by inhibiting the acrosome reaction, said method comprising the step of contacting sperm either at the time of sperm capacitation or at the time of egg fertilization with an effective amount of a bombesin antagonist.

12. The method of claim 11 in which said bombesin antagonist is administered vaginally to a female subject for blocking fertilization.

13. The method of claim 12 in which said bombesin antagonist is administered in a formulation consisting of sponge, foam, jelly, and a biocompatible matrix.

14. The method of claim 11 in which said bombesin antagonist is administered systemically or locally to a male subject for blocking fertilization.

15. The method of claim 14 in which said bombesin antagonist is administered locally.

16. The method of claim 15 in which said bombesin antagonist is administered by implantation of a biodegradable or retrievable polymer formulation in the scrotum.

* * * * *

UNITED STATES PATENT AND TRADEMARK OFFICE
CERTIFICATE OF CORRECTION

PATENT NO. : 5,439,884

DATED : August 8, 1995

INVENTOR(S) : Eliot R. Spindel, Srinivasa R. Nagalla, Srinivasan Vijayaraghavan, and Anthony Archibong It is certified that error appears in the above-identified patent and that said Letters Patent is hereby corrected as shown below:

Column 3, line 19-20, replace "(Note that pseudopeptide bond...)" with --(Note that ψ stands for a pseudopeptide bond...--;

Column 4, line 12, replace "Resaerch" with --Research--;

Column 5, line 10, replace "e-aminobutyric acid" with --α-aminobutyric acid--;

Column 7, line 44, replace "$R_6$ is is H," with --$R_6$ is H--;

Column 11, line 23, replace "Leu-ψ[ψ $CH_2NH$]-Leu" with --Leu-ψ[$CH_2NH$]-Leu--;

Column 11, replace lines 26-32 as follows:

--pGlu-Gln-Trp-Ala-Val-Gly-His-Phe-ψ[$CH_2NH$]-Leu-$NH_2$, pGlu-Gln-Trp-Ala-Val-Gly-His-Leu-ψ[$CH_2NH$]-Leu-$NH_2$, Leu-Met-$NH_2$, pGlu-Gln-Arg-Leu-Gly-Asn-Gln-Trp-Ala-Val-Gly-D-Phe-Leu-Leu-$NH_2$, pGlu-Gln-Arg-Tyr-Gly-Asn-Gln-Trp-Ala-Val-Gly-D-Phe-Leu-Met-$NH_2$, or other peptides were prepared in similar yields in an analogous fashion by appropriately modifying the above procedure.--

UNITED STATES PATENT AND TRADEMARK OFFICE
CERTIFICATE OF CORRECTION

PATENT NO. : 5,439,884

DATED : August 8, 1995

INVENTOR(S) : Eliot R. Spindel, Srinivasa R. Nagalla, Srinivasan Vijayaraghavan, and Anthony Archibong It is certified that error appears in the above-identified patent and that said Letters Patent is hereby corrected as shown below:

Column 12, line 62, replace "0-3.0%" with --0-30%--;

Column 19-20, Sequence Listing, 10th line from the bottom, replace "peptide bond (i.e., $CH_2$.NH instead of CO.NH) between Leu" with the following: --peptide bond (i.e., $CH_2$.NH instead of CO.NH) between Phe--.

Signed and Sealed this

Twenty-first Day of November, 1995

Attest:

BRUCE LEHMAN

*Attesting Officer*    Commissioner of Patents and Trademarks

SEQUENCE LISTING ( 1 ) GENERAL INFORMATION:

( i i i ) NUMBER OF SEQUENCES:5

( 2 ) INFORMATION FOR SEQ ID NO: 1:

( i ) SEQUENCE CHARACTERISTICS:
( A ) LENGTH:14
( B ) TYPE:amino acid
( C ) STRANDEDNESS: Not Relevant
( D ) TOPOLOGY: Not Relevant ( i x ) FEATURE:

(D) OTHER INFORMATION: The sequence contains at position 1 a
pyroglutamate, rather than a glutamate, and has an amide
C-terminus (i.e., CO.NH2), rather than a carboxyl
C-terminus (i.e., CO.OH).

(xi) SEQUENCE DESCRIPTION: SEQ ID NO: 1:

Glu Gln Arg Leu Gly Asn Gln Trp Ala Val Gly His Leu Met
                5                           10

(2) INFORMATION FOR SEQ ID NO: 2:

(i) SEQUENCE CHARACTERISTICS:
      (A) LENGTH:27
      (B) TYPE:amino acid
      (C) STRANDEDNESS: Not Relevant
      (D) TOPOLOGY: Not Relevant    (ix) FEATURE:
      (D) OTHER INFORMATION: The sequence has an amide C-terminus
         (i.e., CO.NH2), rather than a carboxyl C-terminus (i.e.,
         CO.OH).

(xi) SEQUENCE DESCRIPTION: SEQ ID NO: 2:

Ala Pro Val Ser Val Gly Gly Gly Thr Val Leu Ala Lys Met Tyr Pro
                5                           10                          15

Arg Gly Asn His Trp Ala Val Gly His Leu Met
                20                          25

(2) INFORMATION FOR SEQ ID NO: 3:

(i) SEQUENCE CHARACTERISTICS:
      (A) LENGTH:9
      (B) TYPE:amino acid
      (C) STRANDEDNESS: Not Relevant
      (D) TOPOLOGY: Not Relevant    (ix) FEATURE:
      (D) OTHER INFORMATION: The sequence contains at position 1 a
pyroglutamate, rather than a glutamate, has a reduced
peptide bond (i.e., CH2.NH instead of CO.NH) between Leu
and Leu, and has an amide C-terminus (i.e., CO.NH2),
rather than a carboxyl C-terminus (i.e. CO.OH).

(xi) SEQUENCE DESCRIPTION: SEQ ID NO: 3:

Glu Gln Trp Ala Val Gly His Leu Leu
                5

(2) INFORMATION FOR SEQ ID NO: 4:

(i) SEQUENCE CHARACTERISTICS:
      (A) LENGTH:9
      (B) TYPE:amino acid
      (C) STRANDEDNESS: Not Relevant
      (D) TOPOLOGY: Not Relevant    (ix) FEATURE:
      (D) OTHER INFORMATION: The sequence contains at position 1 a
pyroglutamate, rather than a glutamate, has a reduced
peptide bond (i.e., CH2.NH instead of CO.NH) between Leu
and Leu, and has an amide C-terminus (i.e., CO.NH2),
rather than a carboxyl C-terminus (i.e. CO.OH).

(xi) SEQUENCE DESCRIPTION: SEQ ID NO: 4:

Glu Gln Trp Ala Val Gly His Phe Leu
                5

(2) INFORMATION FOR SEQ ID NO: 5:

(i) SEQUENCE CHARACTERISTICS:
      (A) LENGTH:14
      (B) TYPE:amino acid
      (C) STRANDEDNESS: Not Relevant (D) TOPOLOGY: Not Relevant (ix) FEATURE:
(D) OTHER INFORMATION: The sequence contains at position 1 a pyroglutamate, rather than a glutamate, has a reduced peptide bond (i.e., CH2.NH instead of CO.NH) between Leu and Leu, and has an amide C-terminus (i.e., CO.NH2), rather than a carboxyl C-terminus (i.e. CO.OH).

(xi) SEQUENCE DESCRIPTION: SEQ ID NO: 5:

Glu Gln Arg Leu Gly Asn Gln Trp Ala Val Gly His Leu Leu
                  5                        10